United States Patent [19]

Ito et al.

[11] Patent Number: 4,859,077
[45] Date of Patent: Aug. 22, 1989

[54] PRECISION CALORIMETER

[75] Inventors: Shoziro Ito, Setagaya; Akihiro Ito, Tama; Hiroyasu Ito, Niihari, all of Japan

[73] Assignee: Shoziro Ito, Japan

[21] Appl. No.: 87,254

[22] PCT Filed: Dec. 26, 1986

[86] PCT No.: PCT/JP86/00657

§ 371 Date: Jul. 2, 1987

§ 102(e) Date: Jul. 2, 1987

[87] PCT Pub. No.: WO87/03964

PCT Pub. Date: Jul. 2, 1987

[30] Foreign Application Priority Data

Dec. 26, 1985 [JP] Japan .................. 60-294803

[51] Int. Cl.$^4$ .................. G01K 17/00; G01N 25/48
[52] U.S. Cl. .................. 374/33; 422/51; 374/31
[58] Field of Search .................. 374/10–13, 374/33, 34, 31, 32, 36–39; 422/51; 435/291, 12

[56] References Cited

U.S. PATENT DOCUMENTS

| | | | |
|---|---|---|---|
| 2,733,602 | 2/1955 | Jackson et al. | 374/33 |
| 3,392,570 | 7/1968 | Bonjour et al. | 374/11 |
| 4,021,307 | 3/1977 | Mosbach | 435/12 |
| 4,379,775 | 4/1983 | Brandstetr et al. | 374/33 |
| 4,457,252 | 7/1984 | Manske | 374/159 |
| 4,492,480 | 1/1985 | Wadso et al. | 374/12 |
| 4,511,263 | 4/1985 | Prosen | 374/33 |

FOREIGN PATENT DOCUMENTS 3049105 7/1982 Fed. Rep. of Germany ........ 374/31

OTHER PUBLICATIONS

"Bio Activity Monitor," LKB Brochure, No. 2277-00-B-DBE, Oct. 1982.
Nichijo Shinryo ni Yakudatsu "Kanpo Shinryo", vol. 4, No. 5, Oct. 1985, pp. 57–63.
S. Randzio et al., "A Flow Calorimeter with Active Heat Exchangers," J. Phys. E: Scientific Inst., vol. 13, pp. 1292–1296 (1980).
W. Frankvoort et al., "Design and Use of a Dynamic Controlled Adiabatic Liquid-Phase Reaction Calorimeter," J. Phys: E: Sci. Inst. vol. 10, pp. 906–910, (1977).
J. Christensen et al., "An Isothermal Titration Microcalorimeter," The Review of Scientific Instruments, vol. 44, pp. 481–484, (1973).

Primary Examiner—William A. Cuchlinski, Jr.
Assistant Examiner—Patrick R. Scanlon
Attorney, Agent, or Firm—Mason, Fenwick & Lawrence

[57] ABSTRACT

A precision calorimeter which comprises a heater, an agitator and a detection bath which are disposed in a temperature controlled bath and in which gaps formed between them are filled with a liquid; and a detection unit placed in the detection bath, a gap formed therebetween being filled with a liquid; the detection unit being comprised of a detection element, a pipe for passing a sample therethrough provided with a mixer and a reference heater which are arranged between metallic pieces.

2 Claims, 2 Drawing Sheets

PRECISION CALORIMETER

FIELD OF THE INVENTION

The present invention relates to a precision calorimeter and more specifically to an apparatus for determining a small amount of heat generated due to, for instance, thermal reaction of erythrocytes derived from the same origin as that of plasma with plasma which contains cells and is obtained by lightly centrifuging blood, heparin-added blood to removing only erythrocytes therefrom.

BACKGROUND OF THE INVENTION

As the inventor has already reported on Diagnosis and Treatment according to Chinese Medicine (KANPO SHINRYO), October, Showa 60 (1985), p. 57 (issued every two months), the inventor has tried to detect differences in reactivity of living bodies for the purpose of selecting herb medicines. As a result, it has been found that there is a specific relationship between thermal reactions of plasma containing cells, from which only erythrocytes are removed by a light centrifugation of human blood or heparin-added blood with erythrocytes derived from the same origin as that of plasma, sheep blood cells (heterologous erythrocyte) or PHA and diseases.

However, conventional precision calorimeters comprise a detection bath disposed in a temperature controlled bath and a thermocouple and a pipe for passing samples therethrough disposed in the detection bath, the temperature controlled bath being filled with air or water and the detection bath being filled with air. In other words, since the thermocouple is surrounded by an air layer in order to prevent corrosion thereof, there are problems such that it is difficult to control the temperature around the thermocouple and to detect the amount of heat in an accuracy sufficient to conduct the aforementioned medical inspection.

The present invention is directed to the foregoing problems and it is an object of the present invention to provide a precision calorimeter which makes it possible to stably use it for a long period of time without causing corrosion of the portion for detecting quantity of heat, to easily control the temperature within the temperature controlled bath and to detect the amount of heat in a high precision.

DISCLOSURE OF THE INVENTION

The structural characteristics of the precision calorimeter according to the present invention which accomplish the aforementioned object resides in that the calorimeter comprises a heater, an agitator and a detection bath which are disposed within a temperature controlled bath, the gaps formed therebetween being filled with a liquid and that a unit for detection is disposed in the detection bath, the gap therebetween being filled with a liquid and that the detection unit is comprised of a detecting element, a pipe for passing samples therethrough provided with a mixer and a reference heater which are arranged between metallic pieces.

THE MOST PREFERRED EMBODIMENT FOR CARRYING OUT THE INVENTION

Figure 1:
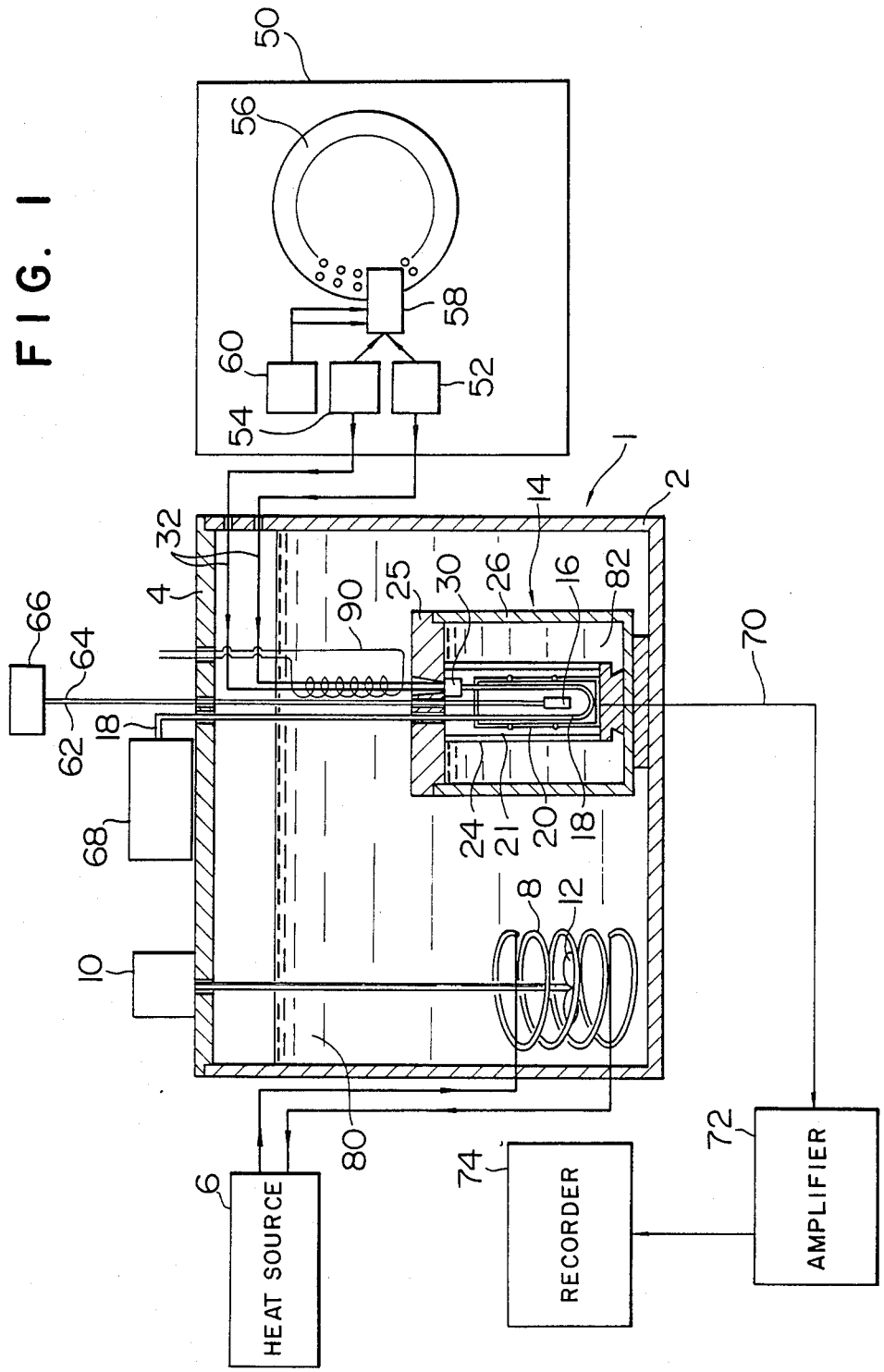
FIG. 1 is a block diagram for explaining an example of the present invention.
Figure 2:
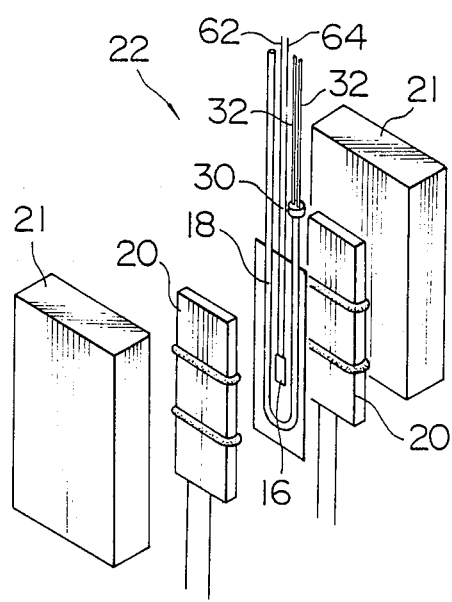
FIG. 2 is an exploded view of the detection present invention; block.
Figure 3:
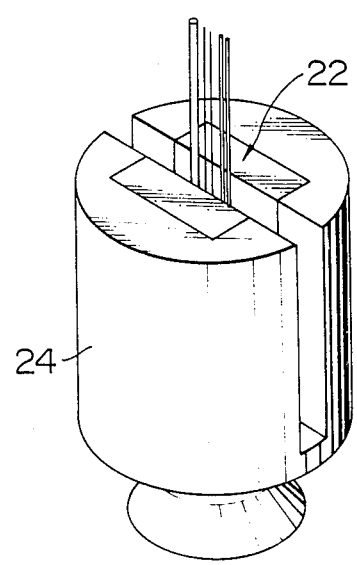
FIG. 3 is a perspective view of an aluminum cylinder.
Figure 4:
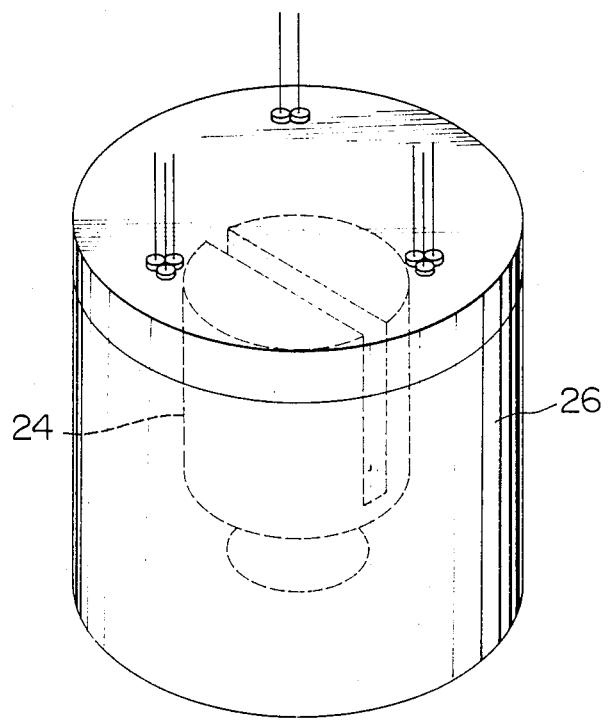
FIG. 4 is a perspective view of the detection unit.

The precision calorimeter of the present invention is explained with reference to the accompanying drawings which show the most preferred embodiment of the present invention. As seen from FIG. 1, the precision calorimeter is constructed by the combination of a temperature controlled bath 2 and a cover 4 which also serves as a bed for placing other elements. In the temperature controlled bath 2, there are arranged a spiral heater 8 which is connected to a heat source 6 disposed outside the bath, an agitator 12 which rotates within the spiral heater 8 by means of a motor 10 placed on the cover 4 and a detection unit 14 and a proper amount of water is introduced in the temperature controlled bath.

The detection unit 14 comprises a detection block 22 which is constructed by putting, between a thermocouple 20, a reference heater 16 consisting of one or a plurality of heating elements and a pipe 18 for passing samples therethrough, which is disposed so as to surround the reference heater and putting these elements between aluminum pieces 21. The detection block 22 is introduced in an aluminum cylinder 24 so as not to form a gap therebetween and the aluminum cylinder 24 is inserted into an aluminum cylinder 26 provided with a cover member 25 so that a gap is maintained between them. The pipe 18 for passing samples therethrough is provided with a mixer 30, which is spaced apart from the reference heater 16 and the thermocouple 20 and is disposed between the aluminum pieces 21, and is communicated with two supply pipes 32 through the mixer 30.

The supply pipes 32 are communicated to liquid pumps 52, 54 of an apparatus 50 for automatically supplying samples which is placed outside the temperature controlled bath 2. The apparatus 50 for supplying samples has the same construction as known ones commercially available and is comprised of a rotatable base 56 for support, an apparatus 58 for withdrawing and air pump 60. The reference heater 16 is connected to power supply 66 therefor through conductive wires 62, 64. The extremity of the pipe 18 for passing the samples therethrough which is not connected to the mixer 30 is communicated to an apparatus 68 for draining the sample.

The thermocouple 20 is connected to an amplifier 72 through a conductive wire 70.

In the foregoing construction, water 80 is introduced into the temperature controlled bath 2, while the aluminum cylinder 26 is filled with one of liquid paraffin, silicone oil and perfluorocarbon 82. In this connection, if the difference between the temperature of water and room temperature is large, the temperature of water situated around the supply pipes 32 becomes low due to the supply of the sample maintained at room temperature and, therefore, it is desirable to dispose a preheater 90 around the supply pipes 32 for the purpose of preventing such temperature difference.

Now, the function of the foregoing example will hereunder be described. First of all, the heat source 6 is started to generate heat from the spiral heater 8, while the agitator 12 is also started to uniformly raise the temperature of the water 80 up to a desired value, for instance, 36° C. Then, the power supply 66 for the reference heater is started to generate heat from the reference heater 16 and thus the thermocouple 20 is calibrated.

Thereafter, the plasma and erythrocytes or the like subjected to a proper treatment are supplied by means of liquid pumps 52, 54 with operating the preheater 90 while taking the difference between the temperature of water 80 and room temperature into consideration. These plasma and erythrocytes or the like are mixed by means of the mixer 30 to form a sample for instrumentation and the sample is supplied through the pipe 18 while causing thermal reaction. On the other hand, the quantity of heat due to the thermal reaction of the sample is detected by the thermocouple 20 as an increase of temperature. The signals thus detected are amplified by the amplifier 72 and are recorded by a recorder 74.

In the precision calorimeter according to the present invention, the temperature control of the detection unit is effected utilizing liquids i.e., water and either liquid paraffin, silicone oil or perfluorocarbon. Therefore, the invention makes it possible to attain effects such that the temperature control is easily and precisely carried out and that precise measurement of the amount of heat generated can be carried out.

In other words, when a conventional precision calorimeter, for instance, LKB (trade name) manufactured in Sweden is used, the measurement of the amount of heat is restricted to 10 to 100 micro W, however, it is demonstrated that the amount of heat up to 0.1 to 1 micro W can stably be determined according to the apparatus of the present invention.

Moreover, in the case where perfluorocarbon surrounds the detection unit, penetration of water into the detection unit can surely be prevented since the specific gravity of the perfluorocarbon is higher than that of water even when the temperature controlled bath is filled with water, according to the precision calorimeter of this invention. Furthermore, the corrosion or oxidation of the thermocouple can thus substantially be reduced.

We claim:

1. A precision calorimeter comprising:
   a temperature-controlled bath container having a heater and an agitator;
   a detection bach container disposed in said temperature-controlled bath container, said detection bath container having a detection unit;
   said temperature-controlled bath container being filled with a liquid having a specific gravity less than the specific gravity of perfluorocarbon, and said detection bath container being filled with perfluorocarbon; and
   said detection unit including a detection element and pipe means for carrying a sample, said pipe means having a mixer and a reference heater, said mixer and said reference heater being positioned between metallic pieces.

2. A precision calorimeter comprising:
   a temperature-controlled bath container having a heater and an agitator;
   a detection bath container disposed in said temperature-controlled bath container, said detection bath container having a detection unit, said detection unit being separated from said detection bath container by a gap, said gap being filled with a liquid; and
   said detection unit including a detection element and pipe means for carrying a sample, said pipe means having a mixer and a reference heater, said mixer and said reference heater being positioned between metallic pieces.

* * * * *